United States Patent
Shapland et al.

(10) Patent No.: US 10,772,901 B2
(45) Date of Patent: Sep. 15, 2020

(54) MEDICINAL COMPOSITION FOR TREATING URINARY TRACT INFECTION (UTI)

(71) Applicants: UROPHARMA LIMITED, London (GB); SYNESIS LLC, Wisconsin Rapids, WI (US)

(72) Inventors: Howard Shapland, Bungay (GB); Scott Glickman, Aylesbury (GB); Christian G. Krueger, Cambridge, WI (US); Amy B. Howell, Hammonton, NJ (US); Jess D. Reed, Madison, WI (US)

(73) Assignees: UroPharma Limited, London (GB); Synesis LLC, Wisconsin Rapids, WI (US)

( * ) Notice: Subject to any disclaimer, the term of this patent is extended or adjusted under 35 U.S.C. 154(b) by 0 days.

(21) Appl. No.: 15/707,605

(22) Filed: Sep. 18, 2017

(65) Prior Publication Data

US 2018/0000853 A1    Jan. 4, 2018

Related U.S. Application Data

(63) Continuation of application No. PCT/EP2016/055933, filed on Mar. 18, 2016.

(60) Provisional application No. 62/294,047, filed on Feb. 11, 2016, provisional application No. 62/135,353, filed on Mar. 19, 2015.

(30) Foreign Application Priority Data

Apr. 17, 2015    (GB) .................................. 1506526.1

(51) Int. Cl.
| | |
|---|---|
| *A61K 31/7028* | (2006.01) |
| *A61K 9/00* | (2006.01) |
| *A61K 31/353* | (2006.01) |
| *A61K 45/06* | (2006.01) |
| *A61K 31/726* | (2006.01) |
| *C07D 311/28* | (2006.01) |

(52) U.S. Cl.
CPC ........ *A61K 31/7028* (2013.01); *A61K 9/0034* (2013.01); *A61K 31/353* (2013.01); *A61K 31/726* (2013.01); *A61K 45/06* (2013.01); *C07D 311/28* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,646,178 A | 7/1997 | Walker et al. | |
| 8,642,088 B2* | 2/2014 | Reed ...................... | A01N 43/16 424/488 |
| 8,715,949 B2 | 5/2014 | Delehanty et al. | |
| 9,040,250 B2 | 5/2015 | Delehanty et al. | |
| 2007/0166409 A1 | 7/2007 | Royds | |
| 2013/0123715 A1 | 5/2013 | Haesaerts et al. | |
| 2014/0010871 A1 | 1/2014 | Mackler | |

FOREIGN PATENT DOCUMENTS

| | | | | |
|---|---|---|---|---|
| CN | 102772499 A | 11/2012 | | |
| EP | 1902721 A1 | 3/2008 | | |
| EP | 2165712 | 9/2011 | | |
| FR | 2874826 B1 | 12/2006 | | |
| RU | 2161446 C2 | 1/2001 | | |
| RU | 2392931 C1 | 6/2010 | | |
| RU | 2405601 C1 | 12/2010 | | |
| RU | 2452535 C1 | 6/2012 | | |
| WO | 1999012541 A1 | 3/1999 | | |
| WO | WO-9912541 A1 * | 3/1999 | ............... | A23L 2/02 |
| WO | 2010078660 A1 | 7/2010 | | |
| WO | 2011088420 A1 | 7/2011 | | |
| WO | WO-2011088420 A1 * | 7/2011 | ........... | A61K 31/352 |
| WO | 2014047221 A1 | 3/2014 | | |

OTHER PUBLICATIONS

Asahara et al., Antimicrobial Agents and Chemotherapy, 2001, vol. 45, No. 6, pp. 1751-1760 (Year: 2001).*
Gupta et al., "Cranberry Products Inhibit Adherence of P-Fimbriated*Escherichia coli* to Primary Cultured Bladder and Vaginal Epithelial Cells", J. Urology, 2007, vol. 177, No. 6, pp. 2357-2360 (Year: 2007).*
Donovan et al., "Procyanidins are not Bioavailable in Rats Fed a Single Meal Containing a Grapeseed Extract or the Procyanidin Dimer B3," Br J Nutr., 87(4):299-306, Apr. 2002.
Jepson et al., "Cranberries for Preventing Urinary Tract Infections," Cochrane Database Syst Rev., Oct. 2012, pp. 82.
Jimenez-Ramsey et al., "Absorption and Distribution of 14C-Labeled Condensed Tannins and Related Sorghum Phenolics in Chickens," J. Agrlc. Food Chem., 42(4):963-967, Apr. 1994.
Pappas et al., "Phytochemicals of Cranberries and Cranberry Products: Characterization, Potential Health Effects, and Processing Stability," Crit Rev Food Sci Nutr., 49(9):741-781, Oct. 2009.

(Continued)

*Primary Examiner* — Jeffrey S Lundgren
*Assistant Examiner* — Michael J Schmitt
(74) *Attorney, Agent, or Firm* — Haukaas Fortius PLLC; Michael H. Haukaas

(57) ABSTRACT

Provided is a pharmaceutical composition for use in a method of preventing or treating a urinary tract infection (UTI), chronic cystitis, overactive bladder, partial bladder obstruction or urethritis, said composition comprising one or more oligomeric tannins, selected from proanthocyanidins and/or hydrolysable tannins, where in said method said composition is administered intraurethrally, intravesically, intraureterally and/or intrarenally, as well as a pharmaceutical composition for use in a method of preventing or treating bladder cancer, where in said method said composition is administered intravesically, said composition comprising one or more oligomeric tannins, selected from proanthocyanidins and/or hydrolysable tannins, wherein said tannins are bound to an anti-cancer agent and/or liposomes containing an anti-cancer agent, together with compositions related thereto.

12 Claims, 8 Drawing Sheets

(56) References Cited

OTHER PUBLICATIONS

Rodriguez-Mateos et al., "Bioavailability, Bioactivity and Impact on Health of Dietary Flavonoids and Related Compounds: An Update," Arch Toxicol., 88:1803-1853, Sep. 2014.

Terrill et al., "Assay and Digestion of 14C-Labelled Condensed Tannins in the Gastrointestinal Tract of Sheep," Br J Nutr., 72(3):467-477, Sep. 1994.

Edens et al., "Oral Administration of Cranberry Juice Cocktail Inhibits *E. coli* 1677 Colonization of the Bladder in a Mouse Model of Urinary Tract Infection," FASEB J., 16(5):A1009, Mar. 2002.

Eydelnant et al., "Cranberry Derived Proanthocyanidins Reduce Bacterial Adhesion to Selected Biomaterials," Langmuir, 24(18):10273-10281, Sep. 2008.

Foo et al., "The Structure of Cranberry Proanthocyanidins which Inhibit Adherence of Uropathogenic P-fimbriated *Escherichia coli* in Vitro," Phytochemistry, 54(2):173-181, May 2000.

Gupta et al., "Inhibition of Adherence of Multi-drug Resistant *E. coli* by Proanthocyanidin," Urol Res., 40(2):143-150, Apr. 2012.

International Search Report and Written Opinion of the ISA/EP dated May 10, 2016 in International Application No. PCT/EP2016/055933; 14pgs.

Jiang, et al. XP002757141; Database WPI, Week 201342; 14(32), Nov. 2012.

Klevens et al., "Estimating Health Care-Associated Infections and Deaths in U.S. Hospitals, 2002," Public Health Rep., 122(2):160-166, Mar.-Apr. 2007.

Ulrey et al., "Cranberry Proanthocyanidins have Anti-biofilm Properties Against Pseudomonas aeruginosa," BMC Complement Altern Med., 14(499):1-12, Dec. 2014.

Howell, A., "Cranberry Proanthocyanidins and the Maintenance of Urinary Tract Health," Crit Rev Food Sci Nutr., 42(3 Suppl):273-278, Feb. 2002.

\* cited by examiner

MEDICINAL COMPOSITION FOR TREATING URINARY TRACT INFECTION (UTI)

RELATED APPLICATIONS

This application is a continuation under 35 U.S.C. 111(a) of International Application No. PCT/EP2016/055933 filed Mar. 18, 2016, which claims priority under 35 U.S.C. § 119(e) to U.S. Provisional Patent Application Nos. 62/135,353, filed Mar. 19, 2015 and 62/294,047, filed Feb. 11, 2016, and which claims priority to Great Britain Patent Application No. 1506526.1, filed Apr. 17, 2015, which applications are incorporated herein by reference.

FIELD OF THE INVENTION

The invention relates to methods of preventing/treating urinary tract infection, chronic cystitis, overactive bladder, partial bladder obstruction, urethritis and bladder cancer, and compositions and devices etc. therefor.

BACKGROUND TO THE INVENTION

Urinary Tract Infection
Preamble

The urinary tract comprises the kidneys, ureters, bladder and urethra. The tract is expected to be normally sterile except for the distal part of the urethra, which has resident bacterial flora. The tract is normally protected from becoming infected by the flushing effect of urinary voiding and immunological mechanisms.

The inner lining of the bladder, the urothelium (which comprises transitional epithelia), has several important functions. It acts as a membrane that essentially prevents urinary constituents from being reabsorbed into the system. It serves to monitor continuously the stretch and temperature of the bladder and monitors for the presence of noxious stimuli, thus it may have a role also therefore in the host's defences against urinary tract inflammation and infections.

A urinary tract infection (UTI) occurs when a part of the urinary tract becomes excessively colonized, usually by bacteria. A UTI can be asymptomatic or can cause symptoms such as lower abdominal discomfort, pain when urinating (dysuria), urgency to pass urine and/or a desire to pass urine excessively frequently. UTIs can progress to serious illness and some can be life threatening.

A variety of bacteria can produce urinary tract infections amongst which are e.g. *Escherichia coli* (*E. coli*), *Klebsiella* spp, *Proteus* spp, *Pseudomonas aeruginosa, Enterococcus faecalis, Staphylococcus, Mycoplasma* sp. and *Chlamydia* sp. Fungi and parasites also can infect the urinary tract. Generally the most common infecting organism is the bacterium *E. coli*, which causes around 85% of these infections.

It has been suggested that some bacteria that enter the bladder can penetrate into the lining urothelial cells where they can take up residence for months and also can multiply within the cells. In addition, it is thought that uropathogenic *E. coli* (UPEC) have fimbriae that enable them to attach to and then penetrate into urothelial cells. By residing intracellularly they render themselves less vulnerable to attack by the host's immune system and also from treatments with antibiotics that are taken orally or delivered systemically e.g. by intramuscular or intravenous injection.

Urinary tract infections are common complications of a variety of pathological conditions and diseases associated with abnormalities of urinary tract structure or function such as may occur with trauma or diseases and damage within the central nervous system or conditions associated with compromise of the immune system. Bacteria can enter the urinary tract through the urethra or, much less commonly, through the bloodstream. Urinary tract infections are much more common in females than in males.

Catheterisation of the urinary bladder, a system used to assist voiding or for monitoring urinary output, is commonly complicated by biofilm formation and catheter-acquired lower urinary tract infections. Biofilm formation within the bladder is a common complication from the use of indwelling catheters.

Some bacteria that enter the bladder can form biofilms on catheters or on the urothelium that lines the bladder cavity. A biofilm can be defined as a microbial sessile community characterised by cells that are irreversibly attached to a substratum or interface or to each other, are embedded in a matrix of extracellular polymeric substances that they have produced and exhibit an altered phenotype with respect to growth rate and gene transcription.

Bacteria within biofilms in the urinary tract tend to be more resistant to antibiotics and host immune systems than free bacteria. Urinary tract biofilms can produce a uniquely challenging problem to clinicians in attempting to eradicate them, because the organisms that make up biofilms may produce urease, an enzyme that hydrolyses urea, to produce free ammonia that raises the pH in the urine. This, in turn, can enable precipitation of minerals such as calcium phosphate or magnesium ammonium phosphate that can then provide another nidus for bacterial colonisation and multiplication.

Epidemiology

Annually in the US, approximately 1.7 million patients acquire hospital-acquired infections (HoAI) and approximately 100,000 will die from these infections, making HoAIs a leading cause of disease and death in the US. Aside from the death toll, the economic burden on the healthcare system is substantial, with the annual direct cost of HoAIs to US Hospitals estimated to be between $28 and $33 billion. Annual direct costs of HoAIs worldwide in Europe, Japan and the developing nations are billions more. This is a worldwide problem that is getting worse with HoAI rates two to five times higher in the developing world; this enormous strain threatens to further compromise already scarce financial and medical resources among the most vulnerable populations.

Many HoAIs are linked to the use of medical devices such as endotracheal tubes, central venous catheters and urinary catheters, with nearly 40% of healthcare associated infections (HeAI) being UTIs, or an estimated 600,000 patients per year in the USA. Catheter associated urinary tract infections (CAUTIs) account for an estimated 90% of these infections.

UTIs are the most common nosocomial infection experienced by patients in United States hospitals and are responsible for significant morbidity and excess hospital costs. In contemporary hospital services, between 15-25% of hospitalized patients receive urinary catheters during their hospital stay. The most important risk factor for developing a catheter-associated UTI is their prolonged use; the urinary catheter provides a breeding ground for bacteria and the slime-like aggregations of bacteria that are biofilms, which are nearly impossible to kill with conventional antibiotics.
Clinical Challenges Antibiotics are the current mainstay treatment for symptomatic UTIs, but their effectiveness can be limited and excessive use of antibiotics to treat UTIs may lead to increased antibiotic resistance in uropathogenic bacteria. This situation is likely to be exacerbated by a foreseeable rise in the number of elderly immunocompromised patients.

An antimicrobial agent without bactericidal or bacteriostatic properties, which are typical properties of antibiotics, that could facilitate the removal of bacteria within the urinary tract without provoking protective mutations in uropathogens with which they come into contact would be considered a useful advance in the prophylaxis and treatment of UTI.

In North America, cranberries, a source of tannins (e.g. proanthocyanidins), have long been considered to have medicinal properties, and cranberry juice has until fairly recently been recommended for prevention and treatment of UTIs. However, clinical studies have yet to provide evidence of therapeutic efficacy in the prevention or treatment of catheter-associated urinary tract infections of either consumption of cranberry juice or extracts packaged in other ways for consumption. In addition, a Cochrane Database Systematic Review update (Jepson R. G., Williams G. and Craig J. C. Cranberries for preventing urinary tract infections. Cochrane Database of Systematic Reviews 2012, 10, Art. No.: CD001321. DOI: 10.1002/14651858.CD001321.pub5) concluded that there is no evidence that oral consumption of cranberry juice decreases the number of symptomatic urinary tract infections in women. They go on to add that the large number of dropouts/withdrawals from some of the trials indicates that cranberry juice may not be acceptable over long periods of time. Furthermore, enteral consumption of proanthocyanidins can contribute to nephrolithiasis (kidney stones) progression and enhance anticoagulation effects of other drugs. It is amongst the objects of the present invention to attempt a solution to these problems.
Other Bladder Pathologies The luminal surface of the transitional epithelia of the urothelium is normally coated in a dense layer of glycosaminoglycans (GAGs). GAGs are long unbranched highly anionic polysaccharides and are retained at the transitional epithelial surface largely via their covalent linkage to a core protein (forming proteoglycans). The GAG layer (also known as the mucous layer) is thought to be important for a range of functions such as promoting urothelial impermeability to bacterial adherence/invasion and shielding the transitional epithelia from irritants. Damage to the GAG layer (and/or the underlying epithelia) can give rise to or contribute to e.g. chronic cystitis, Overactive bladder (OAB), and urethritis, where e.g. damage leads to exposure of the epithelia to substances which cause inflammation and/or pain and/or urge symptoms. Damage caused by partial bladder obstruction can also lead to such symptoms. Other causes of epithelium/GAG-layer damage are varied and include e.g. UTI, trauma and radiotherapy.

Chronic cystitis includes painful bladder syndrome (PBS), also known as interstitial cystitis, irradiation cystitis (usually resulting from radiotherapy), ketamine cystitis, granulomatous cystitis, follicular cystitis, trigonitis (inflammation of the trigone, including urethrotrigonitis, where both the trigone and urethra are affected), or abscess-associated cystitis (where the abscess can arise from e.g. UTI, trauma (e.g. bladder stones, catheterisation) or neurogenic bladder.

Treatment options to date include intravesical administration of so-called GAG layer supplements, which are themselves GAGs (in particular for chronic cystitis and OAB), together with an anti-inflammatory and/or anaesthetic to help manage the symptoms, though outcomes remain moderate. For OAB, anti-muscarinic agents are also employed to help control urge symptoms.
Bladder Cancer Bladder cancer is any cancer arising within the bladder, most commonly carcinoma (i.e. involving the urothelium). It is a common cancer giving rise to serious morbidity and mortality.

Superficial tumors can be removed via transurethral resection and/or immunotherapy using intravesical administration of *Bacillus* Calmette-Guérin (BCG), an attenuated live bovine tuberculosis *bacillus, Mycobacterium bovis*. Other intravesical treatments include Anthracyclines (e.g. doxorubicin, valrubicin) and Mitomycins (e.g. Mitomycin C), especially for BCG-refractory cases. However, success rates can be improved, thereby decreasing progression of bladder cancer to stages where extensive surgical intervention is usually required.

SUMMARY OF THE INVENTION

Accordingly, provided is a pharmaceutical composition for use in a method of preventing or treating a urinary tract infection (UTI), said composition comprising one or more oligomeric tannins, selected from proanthocyanidins and/or hydrolysable tannins, where in said method said composition is administered intraurethrally, intravesically, intraureterally and/or intrarenally. In preferred embodiments the UTI is a uropathogenic *Escherichia coli* infection.

Also provided is a pharmaceutical composition for use in a method of preventing or treating chronic cystitis, overactive bladder, partial bladder obstruction or urethritis, said composition comprising one or more oligomeric tannins, selected from proanthocyanidins and/or hydrolysable tannins, where in said method said composition is administered intraurethrally, intravesically, intraureterally and/or intrarenally. Preferably, the chronic cystitis is painful bladder syndrome (PBS), irradiation cystitis, ketamine cystitis, granulomatous cystitis, follicular cystitis, trigonitis, or abscess-associated cystitis.

In preferred embodiments, said one or more oligomeric tannins comprise one or more proanthocyanidins, preferably wherein said one or more proanthocyanidins comprise one or more proanthocyanidins each with:

(a). at least one A-type interflavan linkage; and/or (b). a flavanol/flavan degree of polymerisation of four or more.

In preferred embodiments, the composition is substantially free of monomeric tannin base units.

In preferred embodiments, the composition additionally comprises one or more additional agents from the group consisting of: an anti-infective agent, an anti-muscarinic agent, an anti-inflammatory agent, an anaesthetic, glycosaminoglycan, and an anti-cancer agent. In specific embodiments thereof, for any additional agent, part or all of the tannins are bound to:
(a). part or all of the additional agent; and/or
(b). liposomes containing part or all of the additional agent.

Also provided is a pharmaceutical composition comprising:
(a). one or more oligomeric tannins, selected from proanthocyanidins and/or hydrolysable tannins; and
(b). one or more additional agents selected from the group consisting of: an anti-infective agent, an anti-muscarinic agent, an anti-inflammatory agent, an anaesthetic, a glycosaminoglycan and/or an anti-cancer agent;
wherein said composition is suitable for intraurethral administration, intravesical administration, intraureteral administration and/or intrarenal administration.

In preferred embodiments, for any additional agent, part or all of the tannins are bound to:
(a). part or all of the additional agent; and/or
(b). liposomes containing part or all of the additional agent.

In preferred embodiments, said one or more oligomeric tannins is as defined above (comprise one or more proanthocyanidins) and/or said composition is substantially free of monomeric tannin base units.

Also provided is a pharmaceutical composition for use in a method of preventing or treating bladder cancer, where in said method said composition is administered intravesically, said composition comprising one or more oligomeric tannins, selected from proanthocyanidins and/or hydrolysable tannins, wherein said tannins are bound to an anti-cancer agent and/or liposomes containing an anti-cancer agent. Preferably, the anti-cancer agent comprises an Anthracycline, a Mitomycin, or *Bacillus* Calmette-Guérin (BCG) and/or the composition additionally comprises one or more additional agents from the group consisting of: an anti-infective agent, an anti-muscarinic agent, an anti-inflammatory agent, an anaesthetic and a glycosaminoglycan.

Also provided is a pharmaceutical composition comprising one or more oligomeric tannins, selected from proanthocyanidins and/or hydrolysable tannins, wherein said tannins are bound to an anti-cancer agent and/or liposomes containing an anti-cancer agent, and wherein said composition is suitable for intravesical administration. Preferably the anti-cancer agent comprises an Anthracycline, a Mitomycin, or *Bacillus* Calmette-Guérin (BCG) and/or the composition additionally comprises one or more additional agents selected from the group consisting of: an anti-infective agent, an anti-muscarinic agent, an anti-inflammatory agent, an anaesthetic and/or a glycosaminoglycan.

Included within the scope of the invention is a pharmaceutical composition for use and a pharmaceutical composition substantially as described herein.

DETAILED DESCRIPTION OF THE INVENTION

Figure 1:
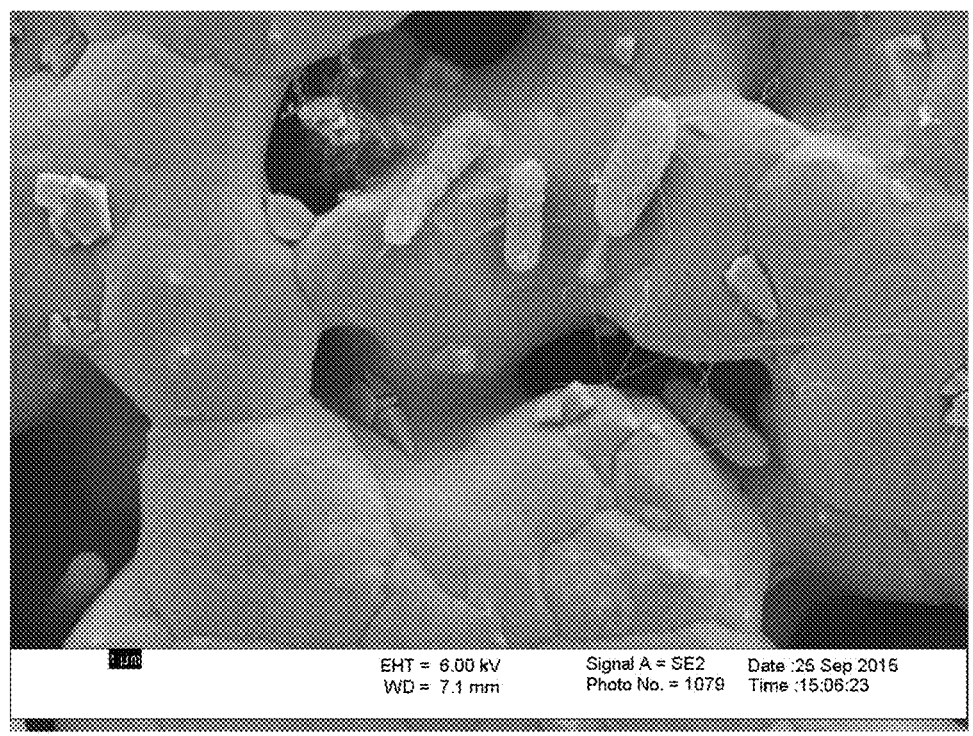
FIG. 1 shows scanning electron microscopy images of immobilised *E. coli* 5011 cells with (bottom panel) and without (top panel) the addition of a tannin composition.
Figure 1:
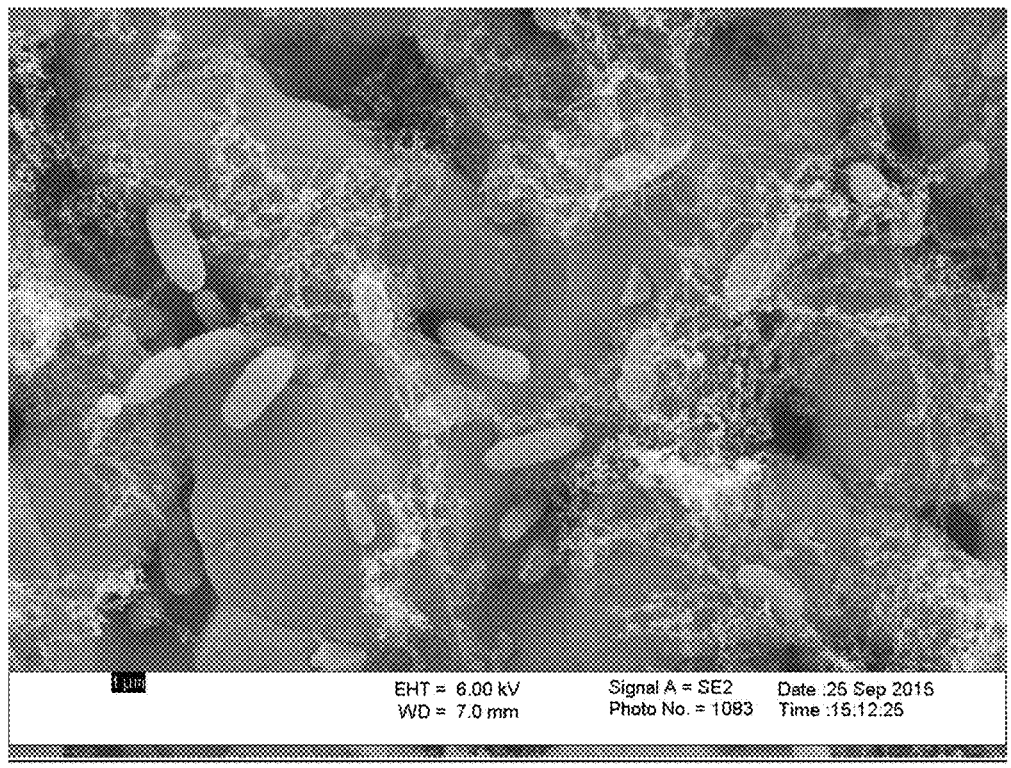

Provided herein are certain pharmaceutical compositions, for use in certain medical indications and per se. 'Pharmaceutical composition' reflects e.g. the clinical setting in which these compositions are intended to be used and this language should not be interpreted as meaning that the claimed compositions must or should be pursued via a particular regulatory approval path (e.g. medicine/pharmaceutical cf device). For example, 'pharmaceutical composition' does not necessarily equate with being or containing an active pharmaceutical ingredient.

The pharmaceutical compositions comprise one or more oligomeric tannins, selected from proanthocyanidins and/or hydrolysable tannins. Pharmaceutically-acceptable salts of these tannins are explicitly contemplated. A plurality of oligomeric tannins (e.g. a plurality of proanthocyanidins) is preferred in order to e.g. minimize the development of resistance in causative agents of UTIs. Oligomeric means comprising two or more (e.g. 2 to 50) monomeric base units (identical or otherwise), and is interchangeable with the term polymeric.

Proanthocyanidins

In the (oligomeric) proanthocyanidins, one or more flavanol and/or flavan base units is/are included. In the simplest case, a flavanol or flavan base unit is linked to a non-flavanol/flavan base unit. However, preferred (oligomeric) proanthocyanidins comprise an oligomer of flavanol and/or flavan base units (with or without a non-flavanol/flavan base unit(s)). In this instance the flavanol and/or flavan base units are linked via one or more interflavan bonds, specifically through one or more B-linkages (4-to-6 or 4-to-8 carbon-carbon bonds) and/or one or more A-linkages (a combination of a 4-to-8 carbon-carbon bond and a C2-to-7 ether bond (i.e. a bond between the C2 of the first unit and the oxygen attached to the C7 of the second unit)).

Preferred proanthocyanidins include the procyanidins, the prodelphinidins, and the propelargonidins. Scheme A illustrates example procyanidins and prodelphinidins (with 4-to-8 B-type linkages). Procyanidins (R=H) contain catechin and/or epicatechin base units; prodelphinidins (R=OH) contain gallocatechin and/or epigallocatechin subunits.

Scheme A.

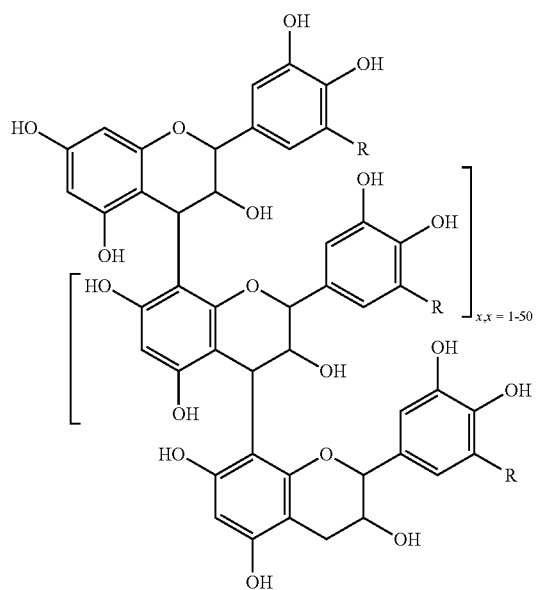

Scheme B.

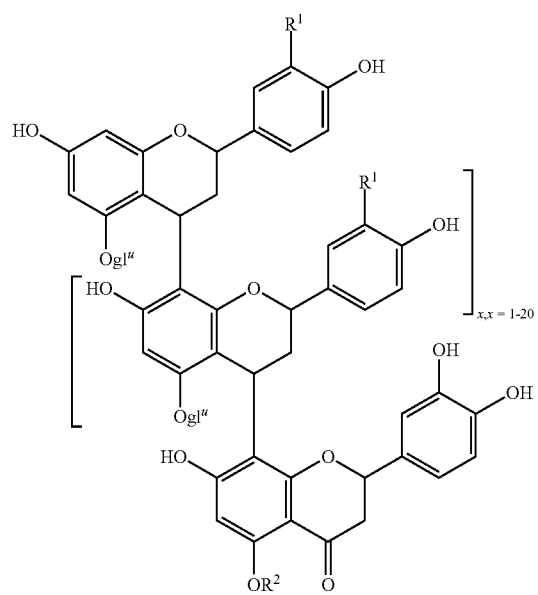

(Note R1 is H or OH; R2 is H or glucose; and glu is glucose (e.g., a β-glucoside).)

Here, the overall degree of polymerisation is the same as the flavanol/flavan degree of polymerisation (and is e.g. 3 [i.e. trimeric] where x=1). Optionally, one or more hydroxyl groups may be absent or may be glycosylated.

Scheme B illustrates other preferred proanthocyanidins, glycosylated heteropolyflavans, particularly using base units of proluteolinidin (R1=OH), proapigininidin (R1=H), eriodictyol (R2=H), and eriodictyol 5-O-β glucoside (R2=glucose).

Where e.g. x=1, the overall degree of polymerisation is 3 [i.e. trimeric] whereas the flavanol/flavan degree of polymerisation is 2 [i.e. dimeric].

Scheme C shows another example preferred proanthocyanidin, a cranberry polyflavan-3-ol, with both A-type and B-type interflavan linkages and substitution to an anthocyanin terminal unit through a $CH_3$—CH bridge.

Scheme C.

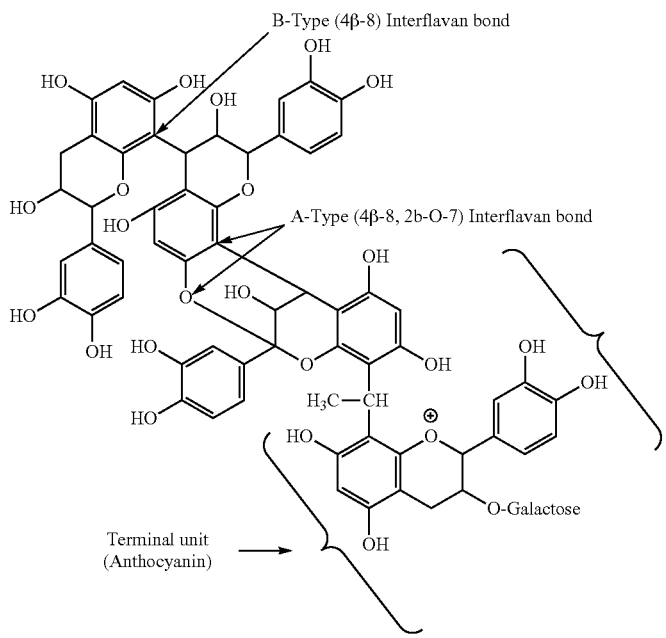

Here, the overall degree of polymerisation is 4 [i.e. tetrameric] whereas the flavanol/flavan degree of polymerisation is 3 [i.e. trimeric].

Examples of plants that produce proanthocyanidins include cranberries, blueberries, grapes, sorghum, cacao and pine.

Hydrolysable Tannins

Additionally, or alternatively, the one or more oligomeric tannins comprise one or more (oligomeric) hydrolysable tannins. Oligomeric hydrolysable tannins comprise two or more (up to e.g. twelve) hydrolysable tannin base units, wherein each such base unit comprises a gallic acid and/or ellagic acid ester of a polyol core moiety (e.g. comprising a sugar or quinic acid).

For example, Scheme D shows an ellagitannin base unit (punicalagin) from pomegranate showing structural variation in the nature of esterification of the glucose core molecule.

Scheme D

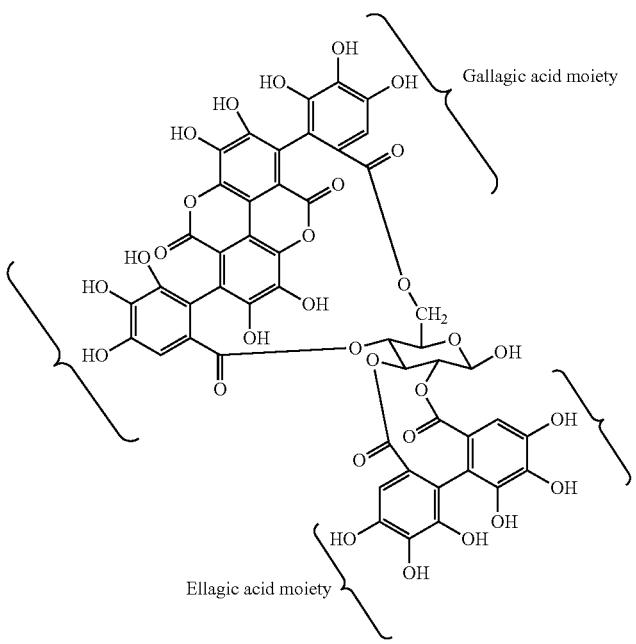

Another preferred tannin base unit is punicalin.

Hydrolysable tannin base units can be linked e.g. by oxidative C—O coupling between galloyl and hexahydroxydiphenoyl moieties of the base units. Linkage can also occur e.g. between two ellagic acid moieties, or by addition of gallic acid moieties to the saccharide core of an oligomer. Thus in some embodiments, oligomeric hydrolysable tannins include at least two saccharide core moieties.

Examples of plants that produce hydrolysable tannins include pomegranates (the husks in particular), strawberries, raspberries, blackberries, and sumac.

Urinary Tract Infection

Provided is a pharmaceutical composition for use in a method of preventing or treating a UTI, said composition comprising one or more oligomeric tannins, selected from proanthocyanidins and/or hydrolysable tannins, where in said method said composition is administered intraurethrally, intravesically, intraureterally and/or intrarenally. Intraurethral administration means administration into the lumen of the urethra. Intravesical administration means administration into the lumen of the bladder, particularly via the urethra, either directly or by passage up the urethra, and/or through a fistula. Intraureteral administration and intrarenal administration means administration into one or both ureters and into one or both kidneys, respectively, usually directly (but via the urethra/fistula and bladder).

In preferred embodiments, the one or more oligomeric tannins comprise one or more proanthocyanidins (also known as non-hydrolysable tannins or condensed tannins). It has been found that proanthocyanidins demonstrate antibacterial properties, especially against UPEC, in in vitro epithelial models, particularly inhibition of adherence of bacterial cells to epithelial cells and of invasion of bacterial cells into epithelial cells. In turn it is proposed that these effects might account for inhibition of biofilm formation and/or increased bacterial agglutination. It is proposed that such properties would assist with the prevention of UTI development, and that such properties would assist with treating a UTI by assisting the host immune defence systems and/or antibiotic treatment. Increased agglutination might also lower the numbers of bacteria available to adhere to/invade the epithelium and/or increase the clearance of bacteria from the urinary tract by voiding of the bladder.

The anti-bacterial properties of proanthocyanidins (particularly anti-adherence, anti-invasion and agglutination) were found to increase with an increase in the number of A-type interflavan linkages therein and with an increase in their degree of flavanol/flavan polymerisation. Accordingly, in preferred embodiments, the said one or more proanthocyanidins comprise one or more proanthocyanidins each with:

(a). at least one A-type interflavan linkage (preferably a plurality thereof); and/or (b). a flavanol/flavan degree of polymerisation of four or more (such as five or more, six or more, seven or more, eight or more, ten or more, twelve or more, and up to e.g. 20, 25 or 50).

Preferably, the one or more proanthocyanidins are in the form of a plant extract, i.e. have been obtained via an extraction process from a plant (such as a plant of the *Vaccinium* genus, such as *V. oxycoccus*, *V. macrocarpon* or *V. corymbosum*).

In preferred embodiments, the composition is substantially or completely free of particular (or all) monomeric tannin base units (also sometimes known as "monomeric tannins") and/or other tannin precursor compounds. Substantially free can mean e.g. less than 5% w/w of the composition, such as less than 1% w/w, less than 0.1% w/w, less than 0.01% w/w, or less than 0.001 w/w. Monomeric tannin base units include flavanols (e.g. [epi][gallo]catechin), flavans and hydrolysable tannin base units (e.g. gallotannins, ellagitannins [e.g. punicalagin, punicalin], tannic acid). Tannin precursor compounds include flavanones, flavones, isoflavones, flavonols, anthocyanins, gallic acid and ellagic acid. In certain embodiments, when the composition comprises one or more oligomeric proanthocyanidins, the composition is substantially or completely free of hydrolysable tannins (e.g. oligomeric hydrolysable tannins). In other embodiments, when the composition comprises one or more oligomeric hydrolysable tannins, the composition is substantially or completely free of proanthocyanidins (e.g. oligomeric proanthocyanidins).

It has now been found that oligomeric tannins can agglutinate bacteria in a dose-dependent manner, via a mechanism that at least involves the oligomeric tannins entrapping the bacteria (perhaps forming a web-like network). Activity is seen at doses as low as parts per million. Furthermore, it has now been found that oligomeric tannins associate with the surface of the transitional epithelia in porcine ex vivo bladder tissue studies (binding to the cell surface and/or integrating into the GAG layer thereon and/or associating with the surface of the GAG layer). This significant insight suggests that oligomeric tannins would be highly effective at preventing/treating UTI (especially of the bladder and/or with intravesical administration), not least because localisation of oligomeric tannins to the surface transitional epithelial surface provides an ideal location for those tannins to effect their (biochemical/molecular) adherence inhibition. In addition, those tannins are likely to form a barrier structure on the epithelia to sterically inhibit bacterial adherence, and indeed invasion of bacteria that manage to adhere. This is particularly the case given the apparent web-like network formed by the tannins. Preliminary studies herein in a porcine ex vivo bladder model indeed suggest that oligomeric tannins do indeed serve to inhibit invasion of UPEC into the transitional epithelia of the porcine bladder.

Delivering the one or more oligomeric tannins intraurethrally, intravesically, intraureterally and/or intrarenally to prevent/treat a UTI enables direct and effective treatment to take place with accurate dosing without exposing the individual to unwanted systemic side-effects.

It has been found that in in vitro culture systems, effective anti-bacterial activity (particularly against UPEC) is seen at a concentration of oligomeric tannins (e.g. one or more proanthocyanidins) of 10-200 µg/ml. Furthermore, new studies herein show that such activity is apparent at 0.1 µg/ml or more (especially against *E. coli* CFT-073), such as 0.5 µm/ml or more (especially against *E. coli* 5011), 1 µg/ml or more, or 5 µg/ml or more, up to 10 µg/ml (optionally not including 10 µg/ml), or at 50 µg/ml or less, or at 100 µg/ml or less. Such concentrations might be suitable for compositions administered directly into the urethra (see below). For compositions administered directly into other parts of the urinary tract (e.g. bladder), an individual dose might provide the one or more oligomeric tannins at between 1 µg and 120 mg (based on e.g. a calculation of 200 µg/ml×600 ml total bladder volume), such as between 6 mg (based on e.g. a calculation of 10 µg/ml×600 ml total bladder volume) and 120 mg. Further optional lower dose limits include 60 µg or more, 300 µg or more, 600 µg or more or 3 mg or more, up to e.g. (and optionally not including) 6 mg. Therefore, with a dose volume of e.g. 10-20 ml, the concentration of the oligomeric tannins in the pharmaceutical composition would be between 3 µg/ml and 12 mg/ml, such as between 0.3 mg/ml and 12 mg/ml. It is envisaged that a plurality of such doses would be administered, sequentially, as part of a prophylactic or (in particular) a treatment regime. For example, multiple doses might be administered in a single 24-hr period. Multiple doses could be administered via a same indwelling catheter or via multiple intermittent catheters.

In preferred embodiments, the UTI to be prevented/treated is a lower UTI (i.e. an infection of the bladder and/or the urethra), particularly a bladder infection, but the UTI can also be an upper UTI (affecting a ureter and/or a kidney). In preferred embodiments the UTI is caused by a bacterium, preferably *E. coli*, more preferably UPEC (typically those that are P-fimbriated), more preferably *E. coli* 5011. In certain embodiments the UTI has arisen (or might arise) from (or during/following) the use of a catheter (intermittent or indwelling) (a "catheter-associated UTI"), or the use of another device inserted into the urethra, such as in a healthcare (e.g. hospital) environment. A preferred patient group is individuals with urinary retention and/or having an indwelling catheter. Preferably, the composition is instilled into a partially or (preferably) a substantially or completely voided bladder.

Preferably, the composition is liquid (e.g. at point of use), from low viscosity (i.e. free-flowing) to high viscosity.

In embodiments the composition can be administered directly into the urethra, e.g. via the use of a syringe, optionally wherein the composition is further passaged up the urethra via subsequent insertion of a device e.g. catheter. In these embodiments the composition preferably has a viscosity of 5 mPa·s or more, more preferably 20 mPa·s or more, more preferably 50 mPa·s or more, more preferably 100 mPa·s or more, more preferably 200 mPa·s or more, more preferably 500 mPa·s or more, more preferably 1000 mPa·s or more, such as 1400 mPa·s or more, and up to 3000 mPa·s or less, such as 2400 mPa·s or less or 2000 mPa·s or less, and preferably the composition is a gel (preferably a hydrogel). These characteristics increase suitability for administration into and/or retention within the urethra and/or passage through the urethra. These embodiments are particular suitable for preventing UTI that might be caused by the introduction of a device into the urethra and/or the movement of infectious agents already resident in the urethra proximally up the urethra. A liquid composition will be able to infiltrate the voids created by folding of the urethra and engage with infectious agents at those voids.

In alternative embodiments the composition can be administered directly into the bladder, ureter(s) and/or kidney(s), preferably using a device such as a catheter. In these embodiments the composition preferably has a viscosity of 500 mPa·s or less, preferably 200 mPa·s or less, more preferably 100 mPa·s or less, such as 50 mPa·s or less, 20 mPa·s or less, 5 mPa·s or less, or 2 mPa·s or less. The volume of the composition is preferably 2 ml or more (particularly for administration to a ureter or kidney), preferably 5 ml or more, more preferably 10 ml or more, such as 20 ml or more or 50 ml or more. These characteristics increase suitability for administration into and/or dispersion within and/or drainage from the bladder, ureter(s) and/or kidney(s).

In preferred embodiments, the composition additionally comprises one or more additional agents from the group consisting of: an anti-infective agent, an anti-muscarinic agent, an anti-inflammatory agent, an anaesthetic, a glycosaminoglycan, and an anti-cancer agent.

An anti-infective agent (such as an anti-bacterial, an anti-fungal or an anti-viral) is intended to increase the effectiveness of the composition against the causative agent of the UTI. In embodiments, particularly where said causative agent is a bacterium (especially UPEC), the anti-infective agent could work synergistically with the one or more oligomeric tannins, given that the latter might serve (by inhibiting adherence and/or invasion and/or biofilm formation) to increase the expose of the causative agent to the anti-infective agent. The anti-infective agent can be an anti-bacterial, which can be bactericidal (such as chlorhexidine e.g. chlorhexidine digluconate), bacteriostatic, or capable of abrogating bacterial infection by some other mechanism, e.g. inhibiting adhesion of bacteria to host cell surfaces. In this respect a preferred class is bacterial anti-adhesive carbohydrates, such as mannose (e.g. D-mannose) or compounds comprising the same (mannosides).

Particularly in settings where an individual is to be (or is being) treated for overactive bladder (OAB) or neurogenic detrusor overactivity (NDO), an anti-muscarinic agent for such conditions (such as atropine or trospium, preferably atropine, particularly atropine sulphate) could be combined with the one or more oligomeric tannins so that UTI co-morbidity can be treated or prevented. This is particularly suitable for compositions administered intraureterally, intrarenally, and/or (in particular) intravesically.

Particularly where the composition is to be administered intraurethrally or intravesically, an anaesthetic (such as lidocaine, e.g. lidocaine HCl) could be combined with the one or more oligomeric tannins to reduce the pain associated with the introduction of the composition and/or any subsequent device into the urethra, and/or to reduce any pain originating from the bladder (e.g. associated with a UTI or one of the conditions mentioned in the paragraph below). In an intraurethral setting it is particularly preferred that the composition comprises the one or more oligomeric tannins, lidocaine HCl and chlorhexidine digluconate.

Particularly in settings where an individual is to be (or is being) treated for cystitis, such as chronic cystitis (see next section), OAB, partial bladder obstruction or urethritis, anti-inflammatory agent for such conditions (such as glucocorticoids) could be combined with the one or more oligomeric tannins so that UTI co-morbidity can be treated or prevented. This is particularly suitable for compositions administered intraurethrally and/or (in particular) intravesically.

In embodiments, the composition further comprises a glycosaminoglycan, to act as a GAG layer supplement. Such supplements are used to repair GAG layer damage and hence treat diseases/conditions associated with such damage, such as chronic cystitis (see next section), OAB, partial bladder obstruction and urethritis. This approach is suitable where UTI co-morbidity is to be treated or prevented, in particular where the underlying GAG layer damage is secondary to the UTI. The glycosaminoglycan (GAG) can comprise a heparin/heparan sulfate GAG (HSGAG), a chondroitin sulfate/dermatan sulfate GAG (CSGAG), a keratan sulfate or a hyaluronic acid, preferably chondroitin sulphate or hyaluronic acid, or pharmaceutically-acceptable salts thereof. This is particularly suitable for compositions administered intraurethrally and/or (in particular) intravesically.

Particularly in settings where an individual is to be (or is being) treated for bladder cancer (as described below), an anti-cancer agent (see below) could be combined with the one or more oligomeric tannins so that UTI co-morbidity can be treated or prevented. This is particularly suitable for compositions administered intravesically.

The finding that oligomeric tannins associate with the surface of the transitional epithelia has the further implication that oligomeric tannins can play a further role in delivering other agents to that surface, such as the aforementioned agents, in particular an anti-infective agent, anti-muscarinic agent, anti-inflammatory agent, glycosaminoglycan or an anti-cancer agent. By directly or indirectly binding oligomeric tannins to one or more of such agents, the tannins can act to deliver such an agent to the transitional epithelial surface, where such agents might have increased efficacy. Such binding can be applied to part or all of the tannins of the composition (i.e. a subset or all of the population of tannin molecules in the composition). This is particularly the case when treating UTI co-morbidity alongside conditions/diseases responsive to an anti-muscarinic agent, anti-inflammatory agent, a glycosaminoglycan, or an anti-cancer agent, where part or (preferably) all of such agents can be bound to oligomeric tannins.

For prevention/treatment of a UTI, oligomeric tannins can be bound to an anti-infective agent, potentially giving rise to a synergistic effect between the two types of compounds on the UTI. In these embodiments it is particularly preferred that (only) part of the tannins is bound to the anti-infective agent, and that (only) part of the anti-infective agent is bound to the tannins. In that way the composition would comprise free tannins that effect anti-infective actions in the urinary tract lumen and at the transitional epithelial surface, as well as a separate anti-infective agent that is both free within the urinary tract lumen and delivered to the transitional epithelial surface.

The oligomeric tannins (or part thereof) can be (directly) bound to the other agent. (This is particularly preferred where e.g. a GAG is the other agent.) The binding can be covalent (e.g. as a result of cross-linking), or non-covalent, such as ionic, H-bonding, dipole-type bonding, or van der Waals interactions.

Alternatively, or in addition, oligomeric tannins (or part thereof) can be (indirectly) bound to the other agent, specifically wherein said tannins are bound to (the exterior of) liposomes containing part or all of the additional agent (i.e. where the additional agent is situated within the internal liposome core). This is particularly preferred where e.g. an API is the other agent (e.g. anti-infective agent, anti-muscarinic agent, anti-inflammatory agent, anaesthetic, or anti-cancer agent) and/or where the other agent is to be transitioned across the urothelium and/or internalised into urothelial cells. Using a (partially or fully) tannin-labelled/coated liposome is a particularly powerful way to deliver agents to (and potentially into/across) the transitional epithelia given e.g. that a vast array of agents (of e.g. varying size and chemical nature) can be easily encapsulated within liposomes (which can then be routinely coated with oligomeric tannins).

Binding between the tannins and the other agent or liposome is preferably at a ratio (on a weight by weight basis) of between 5:95 and 95:5, more preferably between 1:3 and 3:1.

The skilled person will have access to ample published literature describing various ways in which tannins can be bound to other agents and/or liposomes comprising the same, see e.g. U.S. Pat. No. 8,642,088B2.

Regards intravesical administration, in preferred embodiments, the composition is administered via a cathether adapted to deliver a composition intravesically. Such a catheter might for instance comprise separate channels for bladder drainage and for composition instillation, preferably further comprising means to close the bladder drainage channel at the distal end (so that, once the bladder has been drained, the drainage channel can be closed so that instillation of the composition can then take place without flow of the composition out of the bladder via the bladder drainage channel). Suitable devices are described in e.g. GB2448892B and GB2484598B and see in particular the claims therein.

In preferred embodiments, where the UTI is bacterial, the UTI is prevented/treated by inhibiting (reducing or eliminating) adherence of the bacterial cells to uroepithelial cells and/or the invasion of the bacterial cells into uroepithelial cells and/or the formation of the bacterial cells into a biofilm and/or by increasing agglutination of the bacterial cells.

By preventing a UTI we mean e.g. slowing or eliminating the development of UTI as clinically diagnosed or as measured e.g. by any one or more of the associated symptoms such as lower abdominal discomfort, dysuria, urgency to pass urine and/or a desire to pass urine excessively frequently, and/or detection of significant levels of causative agents of UTI in a urine sample.

By treating a UTI we mean e.g. decreasing the severity or eliminating a UTI, as defined e.g. as described above.

Alternative Bladder Pathologies

The finding that oligomeric tannins associate with the surface of the transitional epithelia has yet the further implication that oligomeric tannins can play a separate role in preventing/treating conditions/diseases that are (or might be) at least in part caused by epithelial and/or GAG layer damage/dysfunction, in particular chronic cystitis, OAB, partial bladder obstruction and urethritis. In particular, but without being bound by theory, oligomeric tannins associated with surface of the transitional epithelia may act (as the GAG layer does) to shield the underlying epithelia from stimuli which precipitate such conditions, particularly with respect to the bladder, and/or to aid with the prevention or repair of damage at the epithelial cell surface that can give rise to these various bladder pathologies.

Therefore, also provided is a pharmaceutical composition for use in a method of preventing or treating chronic cystitis, OAB, partial bladder obstruction or urethritis, said composition comprising one or more oligomeric tannins, selected from proanthocyanidins and/or hydrolysable tannins, wherein said method said composition is administered intraurethrally, intravesically, intraureterally and/or intrarenally, in particular intravesically or (e.g. for urethritis) intraurethrally. With regards chronic cystitis, this includes painful bladder syndrome (PBS) (including Hunner's ulcers), irradiation cystitis, ketamine cystitis, granulomatous cystitis, follicular cystitis, trigonitis (including urethrotrigonitis), and abscess-associated cystitis (arising from e.g. UTI, trauma (e.g. bladder stones) or neurogenic bladder).

Administration methodology in these embodiments can be as described above in relation to UTI.

In these embodiments, the composition preferably additionally comprises one or more additional agents from the group consisting of: an anti-infective agent, an anti-muscarinic agent, an anti-inflammatory agent, an anaesthetic, a glycosaminoglycan (which can be as described above), and an anti-cancer agent (which can be as described below).

A glycosaminoglycan (as previously described), like the oligomeric tannins, is intended to act as a GAG layer supplement and hence to increase (perhaps synergistically) the effectiveness of the composition in preventing/treating chronic cystitis, OAB, partial bladder obstruction or urethritis via e.g. dual protection of the transitional epithelia. An anti-inflammatory agent and/or an anaesthetic can alternatively or additionally be included and is intended to tackle the symptoms of these conditions (especially pain).

Alternatively, or in addition, when preventing/treating overactive bladder (OAB) or neurogenic detrusor overactivity (NDO), an anti-muscarinic agent for such conditions could be included to tackle the symptoms of these conditions. Alternatively, or in addition, when preventing/treating bladder cancer, an anti-cancer agent could be included to deal with this co-morbidity.

Particularly in settings where an individual is to receive (or is receiving) prophylaxis or treatment for a UTI, an anti-infective agent (see previous section) could be combined with the one or more oligomeric tannins so that chronic cystitis, OAB, partial bladder obstruction or urethritis co-morbidity can be treated or prevented.

The finding that oligomeric tannins associate with the surface of the transitional epithelia has the further implication that oligomeric tannins can play a further role in delivering other agents to that surface, such as the aforementioned agents, in particular an anti-infective agent, anti-muscarinic agent, anti-inflammatory agent, glycosaminoglycan, or an anti-cancer agent. By directly or indirectly binding oligomeric tannins to one or more of such agents, the tannins can act to deliver such an agent to the transitional epithelial surface, where such agents might have increased efficacy. Such binding can be applied to part or all of the tannins of the composition (i.e. a subset or all of the population of tannin molecules in the composition). For prevention/treatment of chronic cystitis, OAB, partial bladder obstruction or urethritis, oligomeric tannins can be bound to a glycosaminoglycan, potentially giving rise to a synergistic effect between the two types of compounds on the such conditions. In these embodiments, part or all of the tannins can be bound to the glycosaminoglycan, and part or all of the glycosaminoglycan can be bound to the tannins.

Alternatively or in addition, oligomeric tannins can be bound to all or (preferably) part of an anti-infective agent, to prevent or treat UTI co-morbidity, or to part of or (preferably) all of an anti-muscarinic agent, anaesthetic and/or an anti-inflammatory agent to tackle the symptoms of responsive conditions (as described above), or to part of or (preferably) all of an anti-cancer agent to tackle bladder cancer.

Binding methodology in these embodiments can be as described above in relation to UTI.

By preventing chronic cystitis, OAB, partial bladder obstruction or urethritis we mean e.g. slowing or eliminating the development of any such disease/condition as clinically diagnosed or as measured e.g. by any one or more of an associated symptom such as lower abdominal discomfort or pain, dysuria, urgency to pass urine and/or a desire to pass urine excessively frequently, and/or urinary retention.

By treating any such disease/condition we mean e.g. decreasing the severity or eliminating such disease/condition, as defined e.g. as described above.

Pharmaceutical Composition

Also provided is a pharmaceutical composition comprising:
(a). one or more oligomeric tannins, selected from proanthocyanidins and/or hydrolysable tannins; and (b). at least one additional agent selected from the group consisting of: an anti-muscarinic agent, an anti-infective agent and an anti-inflammatory agent (which can be as described above);

wherein said composition is suitable for intravesical administration.

Such suitability can include e.g. being liquid at between 4° C. and 50° C., e.g. between 15° C. and 40° C., and/or being an aqueous solution. Viscosity can be as described above. The pH of the composition should preferably be between 6 and 8, preferably between 6.5 and 7.5.

In some embodiments, for any additional agent, part or all of the tannins are bound to (a) part or all of the additional agent and/or (b) liposomes containing part or all of the additional agent, as described above.

In preferred embodiments, the composition does not comprise a consumable carrier (e.g. a consumable food product).

Bladder Cancer

The finding that oligomeric tannins associate with the surface of the transitional epithelia has the further implication that oligomeric tannins can play a further role in delivering anti-cancer agents to that surface, potentially increasing the potency of such agents for bladder cancer. Also provided therefore is a pharmaceutical composition for use in a method of preventing or treating bladder cancer (e.g. urothelial carcinoma, such as early-stage/superficial urothelial carcinoma), where in said method said composition is administered intravesically, said composition comprising one or more oligomeric tannins, selected from proanthocyanidins and/or hydrolysable tannins, wherein said tannins are bound to an anti-cancer agent and/or liposomes containing an anti-cancer agent.

Tannin composition, administration methods and binding methods can be as described above.

Preferably, the anti-cancer agent comprises an Anthracycline (such as doxorubicin or valrubicin), a Mitomycin (such as Mitomycin C), or *Bacillus* Calmette-Guérin (BCG). Where the anti-cancer agent is an API, e.g. is an Anthracycline or a Mitomycin, the API is preferably contained within a liposome bound to the oligomeric tannins. BCG can be contained within a tannin-bound liposome and/or bound (directly) to oligomeric tannins. The latter can be achieved by coating BCG cells with oligomeric tannins, which will form a web like network around the BCG surface (see above, and Examples).

In embodiments, the composition additionally comprises one or more additional agents from the group consisting of: an anti-infective agent, an anti-muscarinic agent, an anti-inflammatory agent, an anaesthetic and a glycosaminoglycan, and these can be as described above. In these embodiments the anti-infective agent can include free oligomeric tannins (e.g. oligomeric tannins not bound to an anti-cancer agent or (to the exterior of) a liposome).

Note that part or all of any oligomeric tannins present in the composition that are not bound (directly or indirectly) to an anti-cancer agent may be bound to part or all of any additional component (as described above).

Also provided is a pharmaceutical composition (per se) comprising one or more oligomeric tannins, selected from proanthocyanidins and/or hydrolysable tannins, wherein said tannins are bound to an anti-cancer agent and/or liposomes containing an anti-cancer agent, and wherein said composition is suitable for intravesical administration. Such suitability can be as described above. The anti-cancer agent and binding technology can be as described above.

In the above embodiments, the composition can additionally comprise an anti-cancer agent that is not bound to oligomeric tannins, and this anti-cancer agent can be the same as or different to the anti-cancer agent that is bound to oligomeric tannins.

Methods of Treatment

Also provided are methods of treatment corresponding to all of the "composition for use" aspects of the invention detailed above. So, for example, provided is a method of treating a human or animal (preferably mammalian) individual with a pharmaceutical composition comprising (e.g. an effective amount of) one or more oligomeric tannins, selected from proanthocyanidins and/or hydrolysable tannins, said method comprising administering said composition to said individual (e.g. an individual in need thereof) intraurethrally, intravesically, intraureterally and/or intrarenally. This is for example a method of preventing or treating a UTI.

Catheter

Also provided is a catheter comprising an inner and/or outer coating that comprises one or more oligomeric tannins, selected from proanthocyanidins and/or hydrolysable tannins. By inner coating we mean a coating on a lumen-facing surface(s) of the catheter. By outer coating we mean a coating on a surface facing the external environment. The coating can partially or fully coat such surfaces. Preferably the catheter is adapted to deliver a composition intravesically (as detailed above). In this embodiment the oligomeric tannins serve in particular to prevent UTI infection occurring as a result of the use of the catheter. Preferably the coating is an immobilised or fixed material (rather than a fluid material).

Kit

Also provided is a kit comprising:

(a). any pharmaceutical as structurally defined above; and (b). a cathether adapted to deliver a composition intravesically (as detailed above).

The composition could e.g. be comprised within a disposable syringe ready for administration to the bladder via the catheter. The kit might additionally comprise instructions for administering the composition to an individual via the intravesical route (e.g. using the catheter within the kit).

General

Please note that wherever the term 'comprising' is used herein we also contemplate options wherein the terms 'consisting of' or 'consisting essentially of' are used instead.

EXAMPLES

Example 1—Scanning Electron Microscopy

Pathogenic *E. coli* strains (5011 and CFT073 wild type) were prepared for scanning electron microscopy according to the following protocol. 24 hour cultures (top 10% volume media) of each strain were mixed with either a cranberry proanthocyanidin (c-PAC) formulation (80 μg gallic acid equivalents[GAE]/mL) or control solution and allowed to incubate for ~15 minutes at 37° C. The C-PAC formulation (herein merely "c-PAC") is a purified cranberry extract comprising a range of oligomeric PACs, which is at least substantially free of monomeric tannin base units (also sometimes known as "monomeric tannins") i.e. comprising less than 1% w/w of such base units (see e.g. Feliciano et al. Comparison of isolated cranberry (Vaccinium macrocarpon Ait.) proanthocyanidins to catechin and procyanidins A2 and B2 for use as standards in the 4-(dimethylamino)cinnamaldehyde assay. Journal of agricultural and food chemistry 2012; 60(18): 4578-4585). Solution containing bacteria and solutions (either c-PAC or control) were then fixed with a 3% glutaraldehyde prior to being passed through a 0.45 μm silver membrane filter. The bacteria, now bound to the filter, were stored in 3% glutaraldehyde at 4° C. until prepared for imaging.

Membranes were prepared for imaging by the following protocols. The filters were dehydrated for 15 minutes/series through an ethanol series using the following percentages: 30, 50, 70, 80, 90, 95, 100(×2). The filters were then 100% Sieve dried. The filters were dried via the critical point procedure (10 minutes×3 soaks) and adhered to aluminium SEM specimen stub with double sided carbon sticky tabs. The filters were then sputter coated with a ~25 nm layer of gold/palladium. SEM images were acquired with a Zeiss instrument using an accelerating voltage at 3-10 keV.

Figure 2:
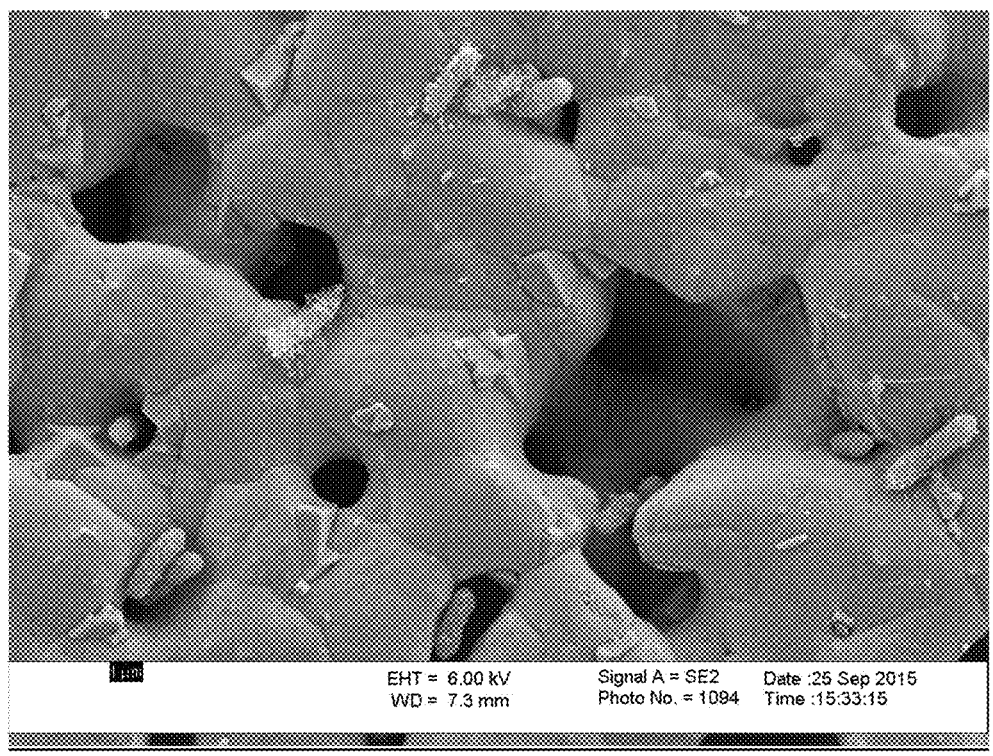
FIG. 2 shows scanning electron microscopy images of immobilised *E. coli* CFT-073 cells with (bottom panel) and without (top panel) the addition of a tannin composition.
Figure 2:
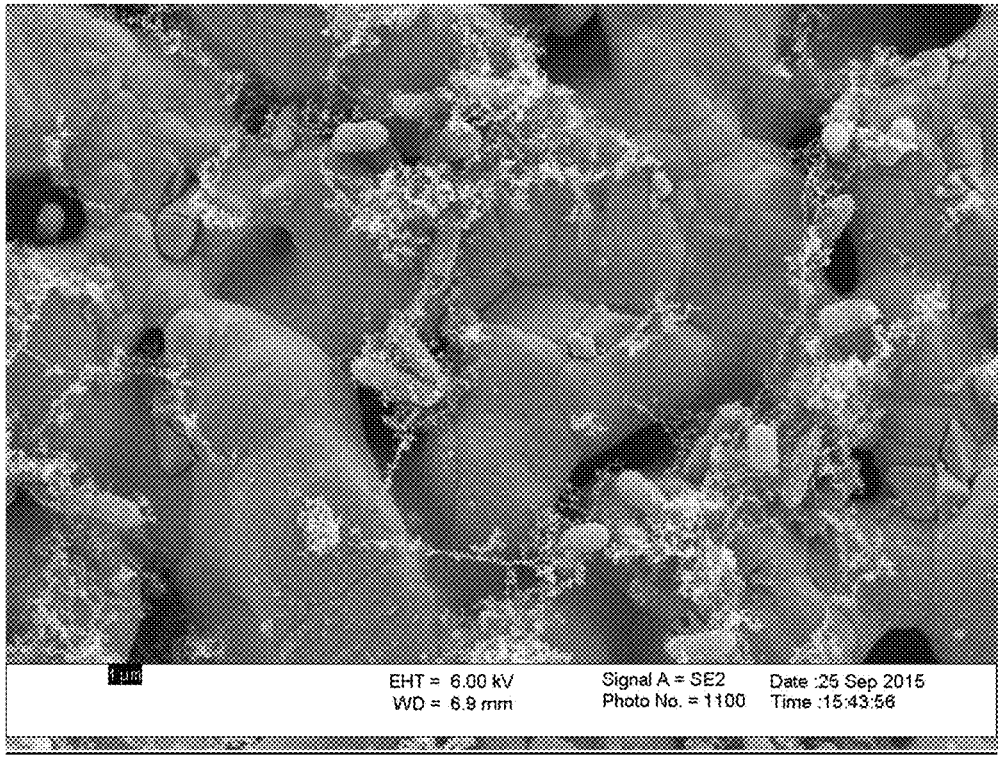

Representative images of bacteria (5011 and CFT073) with and without addition of c-PAC are shown in FIGS. 1 and 2. Images show that 5011 expresses surfaces structures that resemble long polar fimbria (FIG. 1, top panel) and that the addition of c-PAC results in a web like network that appears to physically entrap the bacteria (FIG. 1, bottom panel). Images show that CTF073 expresses surfaces structures that are quite different in morphology than 5011 (FIG. 2, top panel) and that the addition of c-PAC results in a web like network that appears to physically entrap the bacteria (FIG. 2, bottom panel).

Example 2—Agglutination Studies

Pathogenic *E. coli* strains (5011 and CFT073 wild type) were cultured from frozen stock under static conditions in LB broth at 37° C. and washed 2× with PBS++ by centrifugation at 1800×g for 10 minutes. The OD450 was used to calculate and adjust the bacterial cell density using a previously established bacterial density-absorbance curve.

Figure 3:
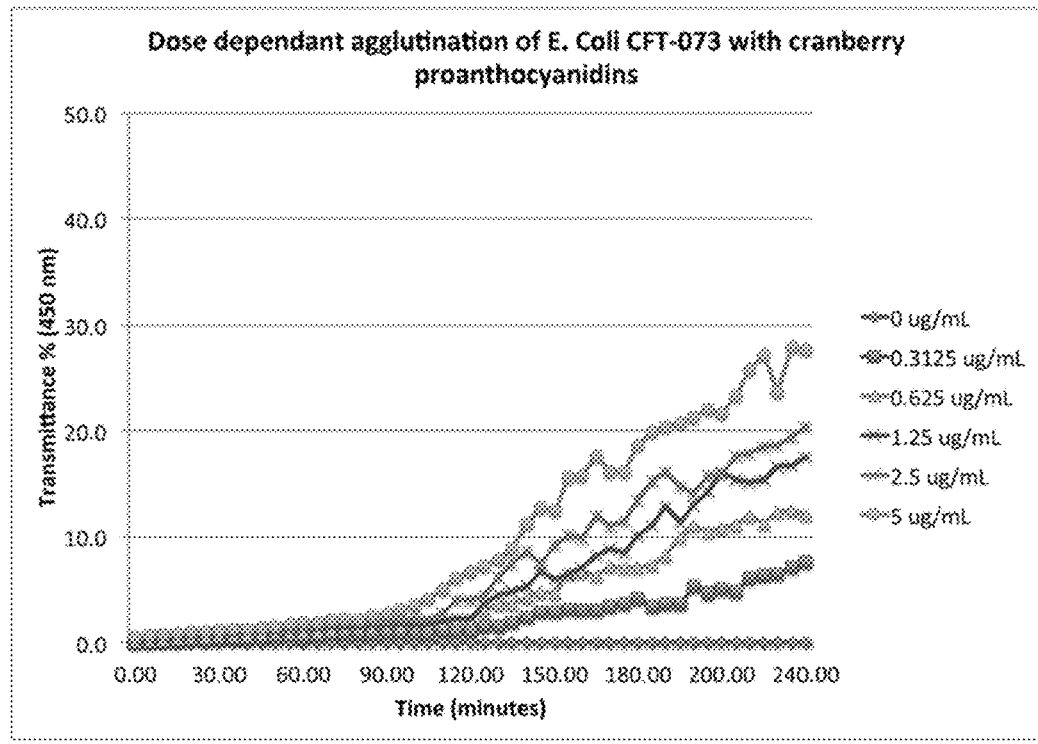
FIG. 3 shows, for *E. coli* CFT073 (top) and 5011 (bottom), agglutination (as measured by increase in transmittance) over time in response to varying concentrations of a tannin composition.
Figure 3:
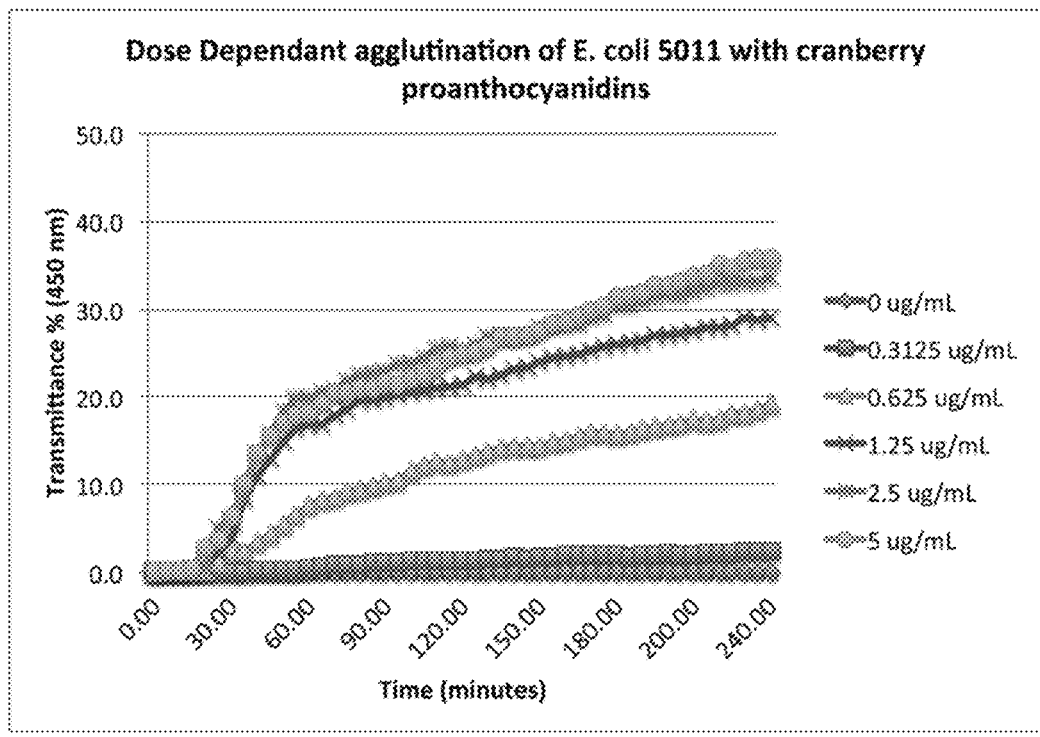

The agglutination assay was conducted in 3.0 mL microcuvettes using 1.0 mL total reaction volume. First, pathogenic *E. coli* stock solutions (50 μL) were added to the cuvettes, resulting in a final concentration of 5.0e^8 colony forming units (CFU)/mL. Next, c-PAC was diluted 1/1000 and added to each bacterial inoculum to reach final concentrations of 0, 0.3125, 0.625, 1.25, 2.5, and 5 μg GAE/mL in a total volume of 1 mL with PBS++. The cuvettes were triturated vigorously for ~10 seconds. Absorbance was read at 450 nm every 5 min for 240 min on a Beckman DU 640 spectrophotometer equipped with a six-position cuvette holder, and the absolute absorbance values were converted to transmittance (%) (FIG. 3). It is noted that c-PAC demonstrates particularly rapid agglutination of *E. coli* 5011, which is a model strain for UTI infection (being a clinically isolated strain from patient urine, compared with CFT-073, which was isolated from patient blood), although a concentration of above 0.3125 μg/ml (e.g. 0.5 μg/ml or more) might be required.

Figure 4:
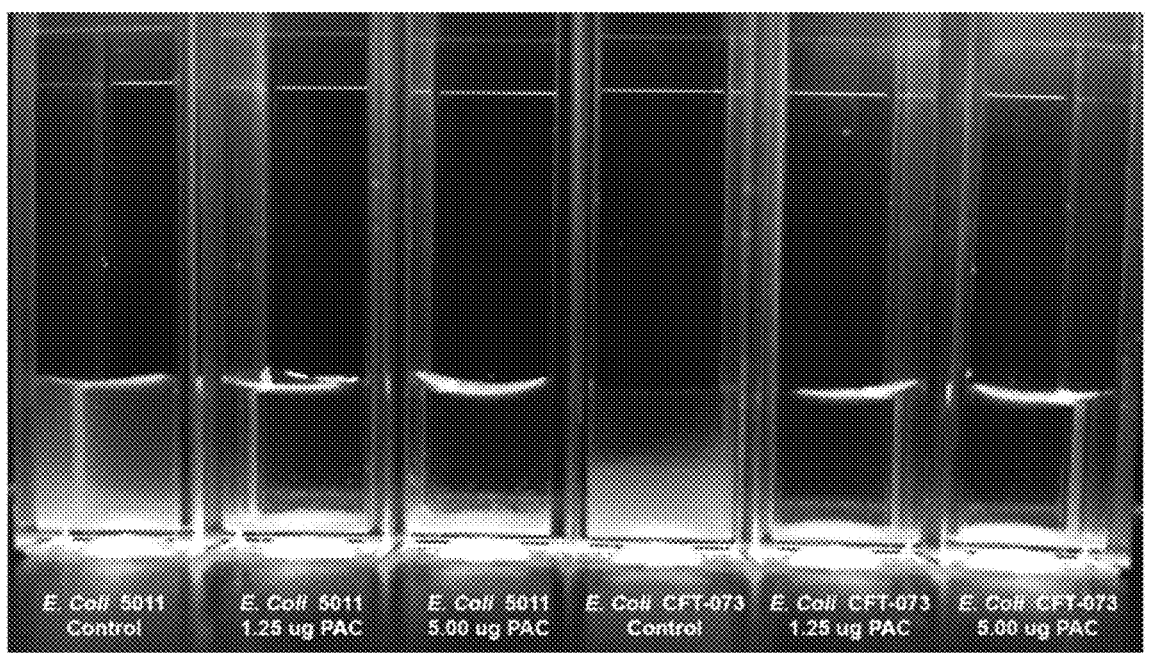
FIG. 4 shows a photograph showing agglutination of *E. coli* 5011 and CFT073 after 19 hours of incubation with a control solution or with a tannin composition at 1.25 µg/ml ("1.25 ug PAC") or at 5 µg/ml ("5.00 ug PAC").

In a separate study c-PAC concentrations of 0, 1.25 and 5 μg were added to *E. coli* strains (5011 and CFT073) and allowed to interact for 19 hours. FIG. 4 shows representative outcome of 5011 and CFT073 being agglutinated and falling out of solution after 19 hours of co-incubation.

Example 3—Microscopy Studies

Figure 5:
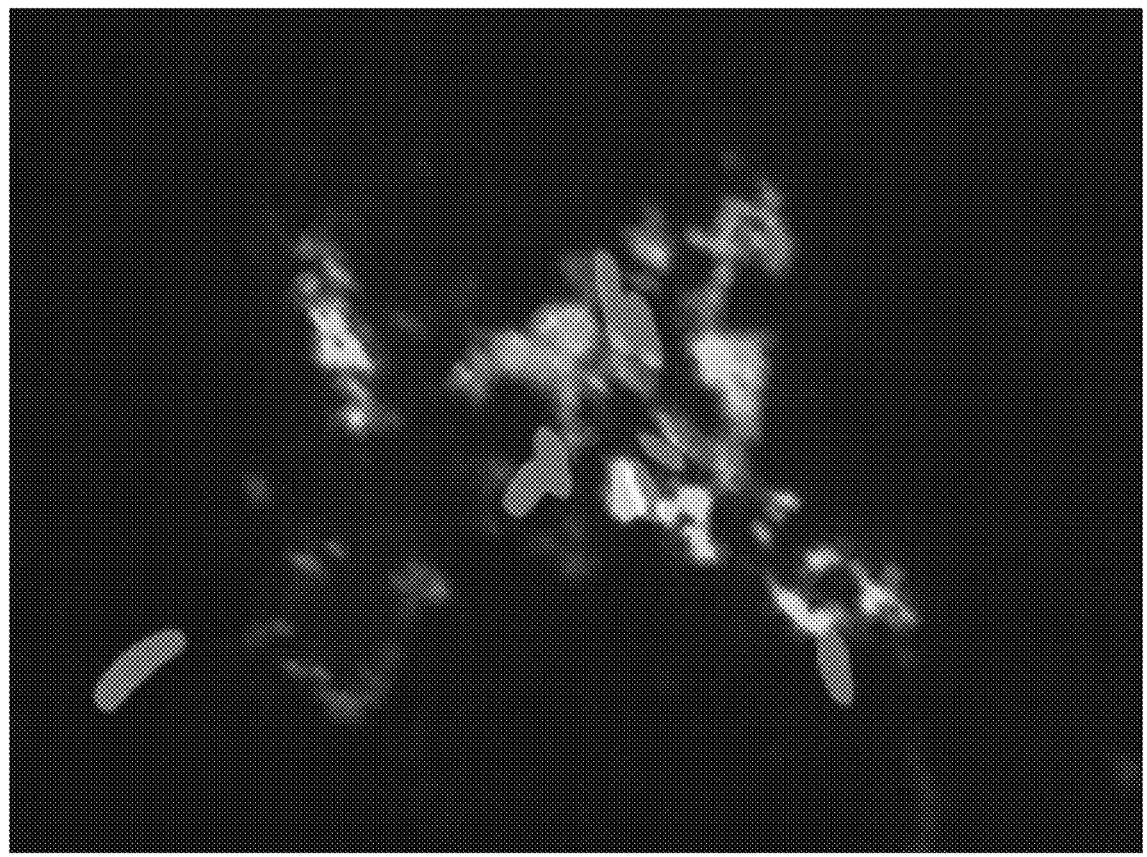
FIG. 5 shows a fluoroscopy image of DTAF-labelled tannins with mCherry-labelled *E. coli* CFT-073.

Bladder tissue samples were obtained as described in the Bladder Tissue Model section (see below) and each section placed (epithelial surface facing up) in individual wells of a 24-well culture plate. CFT073 *E. coli* expressing mCherry were cultured as described as above. Fluorescently labelled c-PAC, 5-([4,6-dichlorotriazin-2-yl]amino)fluorescein (DTAF) was prepared as described by Feliciano et al (Food Chemistry; 166: 337, 2015). The DTAF-labelled c-PAC was combined with CFT073 (mCherry), allowed to co-incubate 10 minutes and were imaged by fluorescent microscopy (FIG. 5; the DTAF-labelled PACs (bright netlike structure) entrap mCherry-labelled pathogenic *E. coli* CFT073 (grey rod shaped structures)). The DTAF-labelled c-PAC in PBS (1 ml) was added to the bladder tissue samples (80, 160, 320, 640, 1280 μg GAE/ml) and incubated for 1 hour in the dark. The DTAF-c-PAC solution was removed, the tissue was then washed with PBS (4×) to remove excess free DTAF-c-PAC and fixed overnight with neutral buffered formalin. The fixed tissue was then dehydrated, embedded in paraffin and mounted on a slide.

Slides where de-paraffinized via the following methodology:
3×5 min Xylenes
10 dips in 100% EtOH
10 dips in 100% EtOH
10 dips in 95% EtOH
10 dips in 50% EtOH
10 dips in 1 distilled $H_2O$
slides were allowed to sit in distilled $H_2O$ for ~5 minutes while the DAPI was prepped.

The slide was next counter stained with 4',6-diamidino-2-phenylindole (DAPI), a fluorescent stain that binds strongly to DNA DAPI prep:

A 1 mg/mL (3.6 mM) DAPI stock solution (in water) was used. The stock solution was diluted 1:100 with $ddH_2O$ (making at 0.036 mM solution). 400 μL of this solution was added to 5 mL of PBS to make a 2.86 uM working concentration of DAPI. This is the solution that was applied to the de-paraffinized slides. Tissue sections were placed on a slide rack and surrounded with a hydrophobic barrier. DAPI was applied with a transfer pipet so that all the tissue was covered. Slides were allowed to stain for 5 minutes in the dark. After the incubation, DAPI was removed and washed with $ddH_2O$. Slides were then mounted with Fluoro Gel (from EMS), covered with a coverslip, and allowed to dry. The slide preparations were imaged by light and fluorescent microscopy (see FIGS. 6 and 7).

Figure 6:
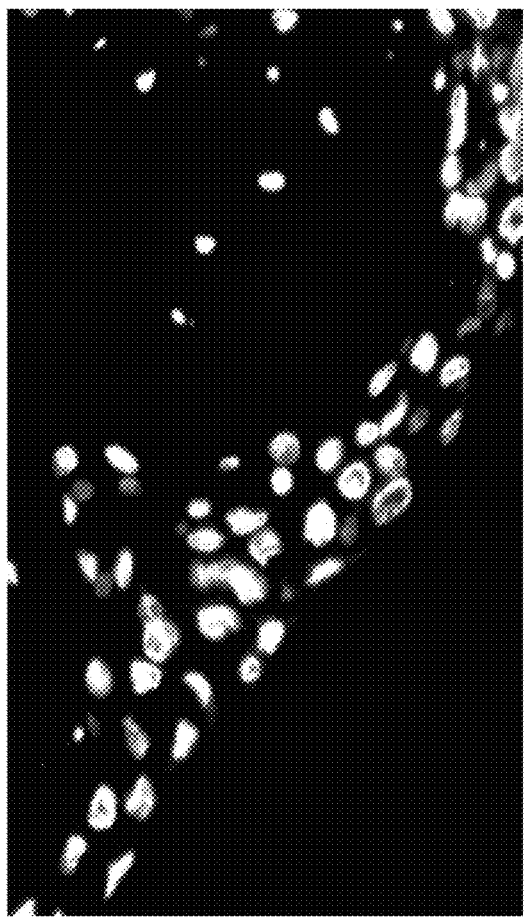
FIG. 6 shows microscopy images of an ex vivo bladder tissue segment, with DTAF-labelled tannins using fluoroscopy (top left), DAPI-labelled nuclei using fluoroscopy (top right), bright field view (bottom left), and composite image (lower right).
Figure 6:
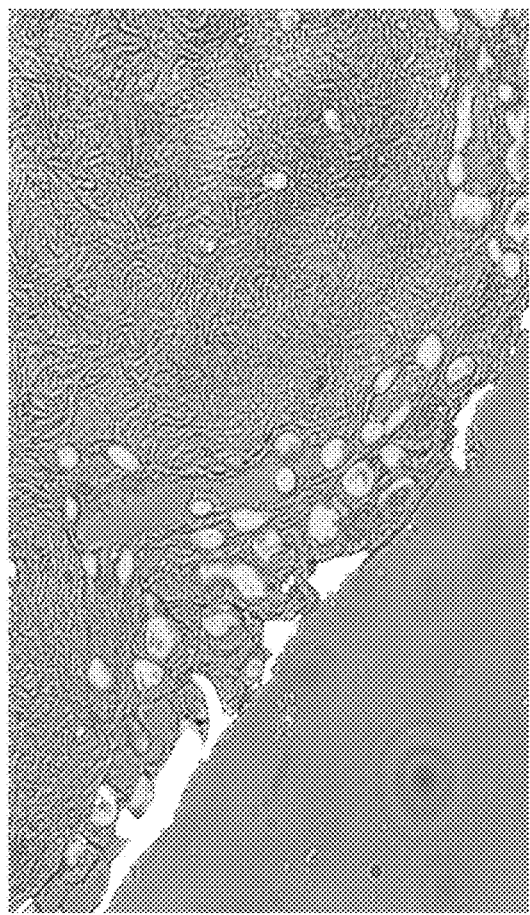
Figure 6:
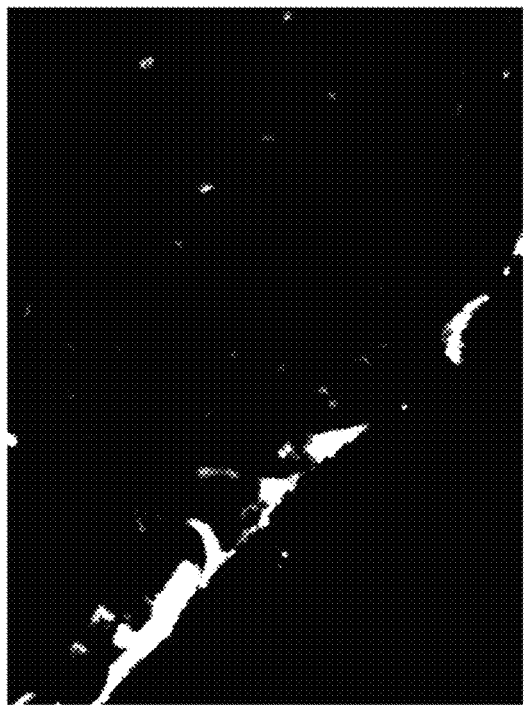
Figure 6:

FIG. 6 shows microscopy images with DTAF-labelled c-PAC using fluoroscopy (bright white, top left) (at 640 μg GAE/ml), DAPI-labelled nuclei using fluoroscopy (light grey, top right), bright field view (bottom left), and composite image (lower right). PACs form a barrier by associating with (perhaps incorporating into) the GAG layer of the transitional epithelial cell surface (granular grey structure with light grey DAPI-labelled nuclei).

Figure 7:
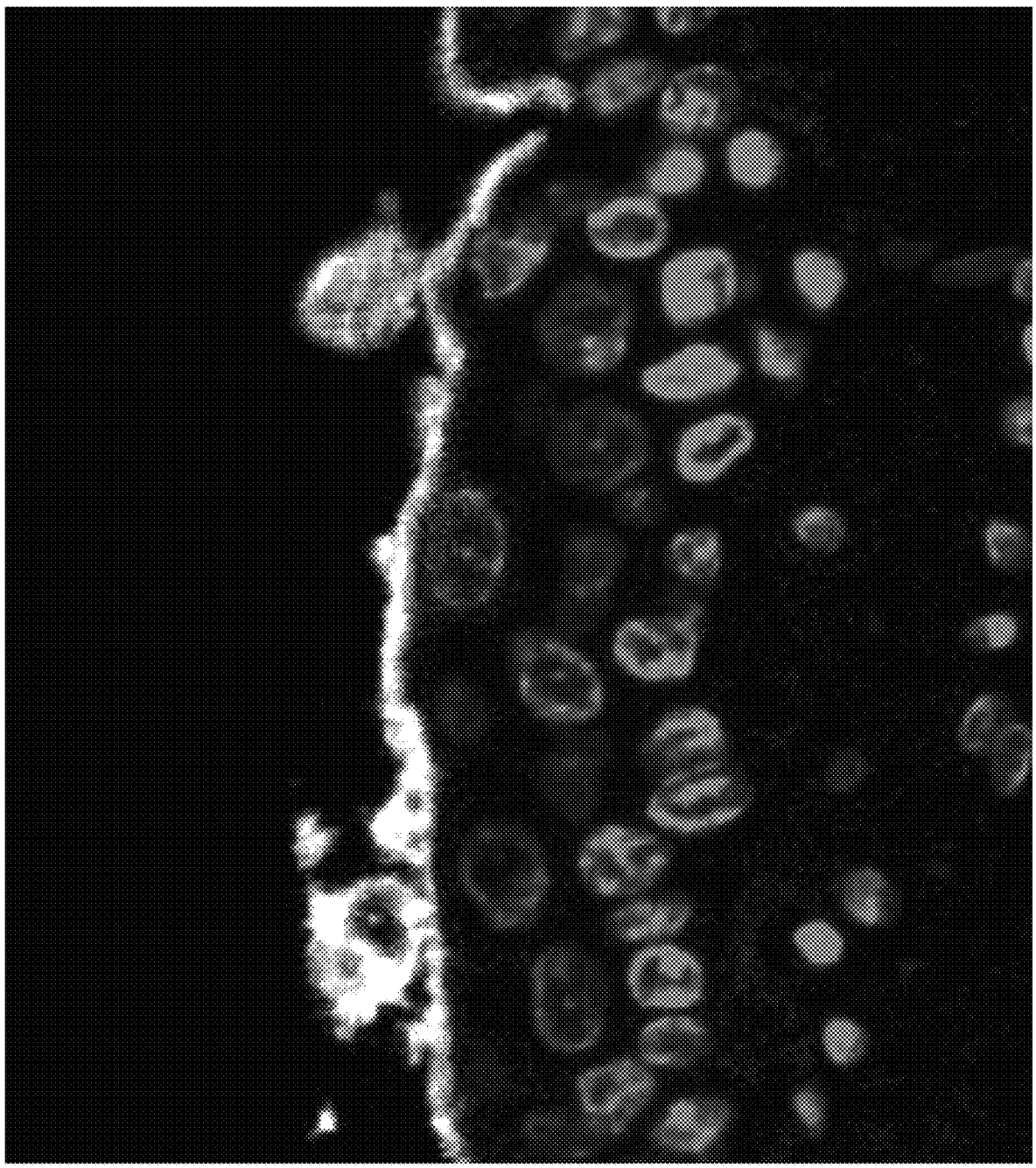
FIG. 7 shows a magnified, composite fluoroscopy image of an ex vivo bladder tissue segment showing DTAF-labelled tannins and DAPI-labelled nuclei.

FIG. 7 shows a magnified, composite fluoroscopy image showing the DTAF-labelled c-PAC (bright white) forming a barrier by associating with/incorporating into the GAG layer of the transitional epithelial cell surface (defined by light grey DAPI-labelled nuclei).

Example 4—Ex Vivo Porcine Bladder Tissue Model

Figure 8:
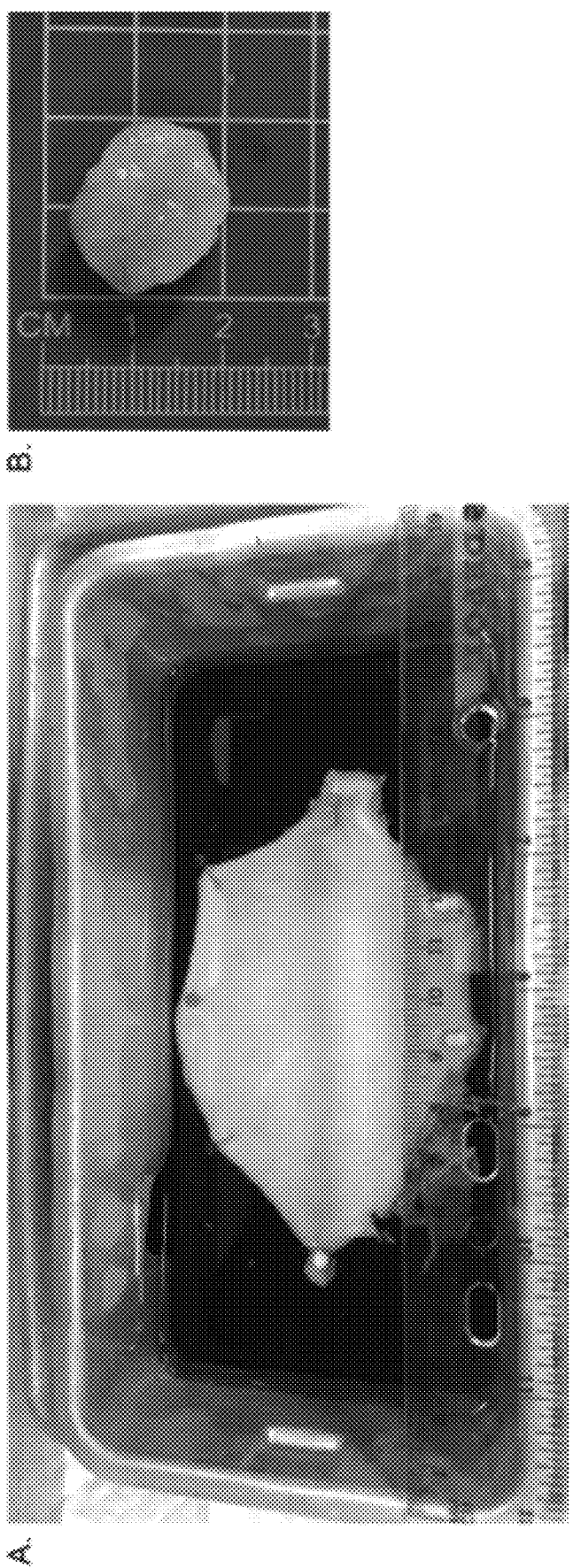
FIG. 8 shows A. a dissected and bisected porcine bladder pinned to silicone coated tray and B. a representative punch from such a bladder that is glued to the bottom of a tissue culture assay plate.

Bladder from porcine were obtained from a local abattoir and transferred back to the lab on ice. Once at the lab, bladders were opened and examined for pathology. Bladders to be used in the invasion assay were washed with PBS, bisected, and pinned down on silicon trays (see FIG. 8A). Bladder sections for use in the bladder invasion assay were punched from the bladder using a round cork-bore (size 11), and measured approximately 1.9 cm² (see FIG. 8B). These bladder sections were then glued to the bottom of a 24-well tissue culture plate and covered with PBS until the 24-well plate was filled with desired amount of bladder sections. Once prepared, the tissue was rinsed with Invasion Media and placed at 37° C./5% $CO_2$ while the bacteria and c-PAC were being prepared.

Pathogenic *E. coli* strain (5011) was prepared for use in an anti-invasion assay according to the following protocol. 72 hour cultures of each strain were diluted to reach varying Multiplicities of Infection (MOI). The MOI is the ratio of bacterial cells to mammalian cells. A MOI curve ranging from 8e2-8e7 CFUs/well was tested to obtain a suitable MOI that could be used in future experiments. The results of these experiments indicated that an MOI of 8e6 is appropriate for testing c-PAC inhibition of invasion.

Figure 9:
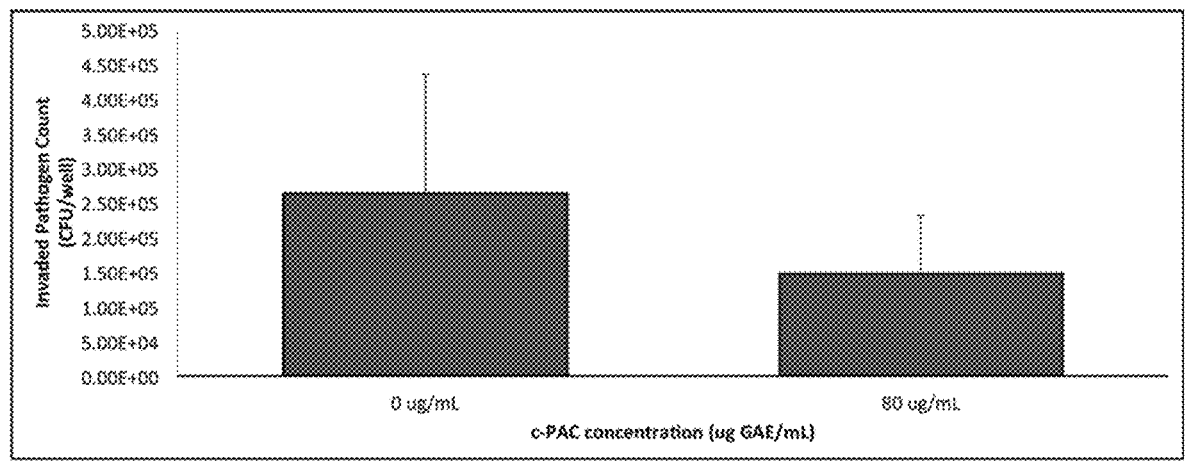
FIG. 9 shows invaded pathogen count against concentration of a tannin composition for a first bladder (top) and a second bladder (bottom) in an ex vivo bladder tissue segment experiment.
Figure 9:
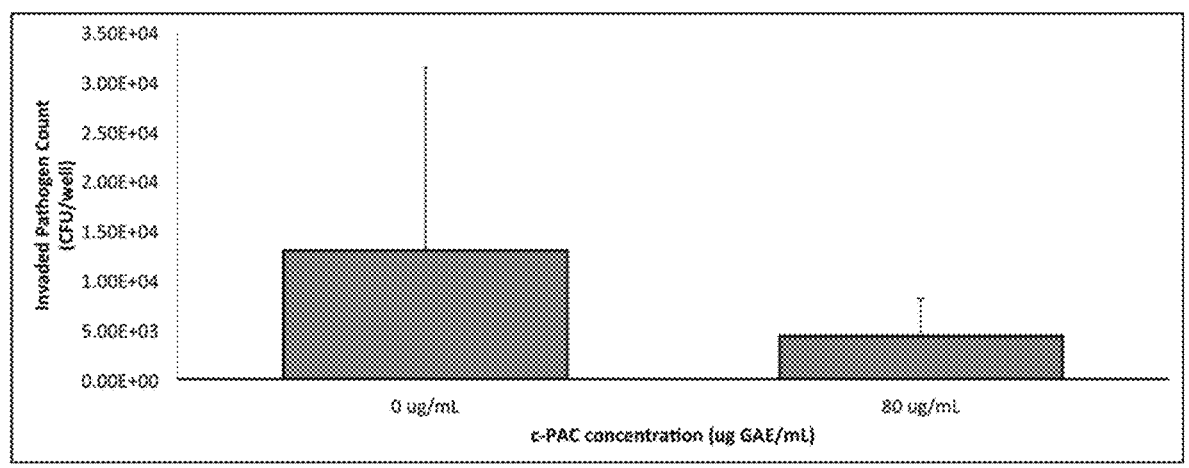

Pathogenic *E. coli* strain (5011 wild type) was prepared for use in an anti-invasion assay according to the following protocol. A 72-hour culture of the strain was mixed with either c-PAC (concentration of 80 mg GAE/mL) or control (0 mg GAE/mL) solution and allowed to incubate for ~15 minutes at 37° C. Solution containing bacteria and treatment (either c-PAC or control) were then applied to porcine bladder tissue for 1 hour at 37° C. and 5% CO2 to allow for bacterial invasion. After the 1-hour treatment, bladder tissue was washed and gentamicin was applied to the tissue for 1 hour at 37° C. and 5% CO2 to allow for the killing of adhered but not invaded bacteria. Tissue was then washed and lysed to liberate the invaded bacteria. Invaded bacteria were plated for enumeration and counted to determine invaded pathogens per well. The results (see FIG. 9) indicate that c-PAC has an inhibitory effect on bacterial invasion.

What is claimed is:

1. A method for treating or inhibiting a urinary tract infection (UTI) in a subject, comprising administering to the subject in need thereof an effective amount of a composition consisting essentially of proanthocyanidins, wherein the composition is administered intraurethrally, intravesically, intraureterally and/or intrarenally, and wherein the proanthocyanidins form a web-like prophylactic network on the epithelial surface of the urogenital tract that agglutinates bacteria by entrapment, thereby promoting urothelial impermeability to bacterial adherence or bacterial invasion;

wherein the proanthocyanidins are oligomeric proanthocyanidins having a flavanol/flavan degree of polymerization of 4 to 25;

the composition is substantially free of monomeric tannin base units and monomeric polyphenols; and the composition administered to the epithelial surface of the urogenital tract has a concentration of proanthocyanidins of about 0.3125 microgram per milliliter to about 5 microgram per milliliter.

2. The method according to claim 1 wherein the UTI is a uropathogenic *Escherichia coli* infection.

3. The method according to claim 1 wherein the proanthocyanidins each have:

(a) at least one A-type interflavan linkage; and
(b) a flavanol/flavan degree of polymerization of 4 to 20; or
(c) an overall degree of polymerization of 4 to 20.

4. The method according to claim 1 wherein the proanthocyanidins have an overall degree of polymerization of 4 to 20.

5. The method according to claim 1 wherein the proanthocyanidins consist of oligomeric proanthocyanidins having an overall degree of polymerization of 4 to 20.

6. A method for treating or inhibiting a urinary tract infection in a subject comprising administering, intraurethrally, intravesically, intraureterally or intrarenally, to a subject in need thereof an effective amount of a composition comprising oligomeric proanthocyanidins, each oligomeric proanthocyanidin having an overall degree of polymerization of 4 to 25;

wherein the composition is substantially free of monomeric tannin base units and monomeric polyphenols, thereby treating or inhibiting the urinary tract infection.

7. The method of claim 6 wherein the composition administered to the subject has a concentration of proanthocyanidins of 0.3125 microgram per milliliter to 5 microgram per milliliter.

8. The method of claim 6 wherein the UTI is a uropathogenic *Escherichia coli* infection.

9. The method according to claim 6 wherein the composition comprising oligomeric proanthocyanidins further comprises one or more hydrolysable tannins.

10. The method according to claim 6 wherein the composition additionally comprises one or more additional agents selected from the group consisting of an anti-infective agent, an anti-muscarinic agent, an anti-inflammatory agent, an anesthetic, a glycosaminoglycan, and an anti-cancer agent.

11. The method according to claim 10 wherein, for any additional agent, part or all of the proanthocyanidins are bound to:

(a) part or all of the additional agent; and/or
(b) liposomes containing part or all of the additional agent.

12. A method for treating or inhibiting a urinary tract infection in a subject comprising administering intraurethrally to the bladder of a subject in need thereof an effective amount of a composition of oligomeric proanthocyanidins;

wherein:
the composition of oligomeric proanthocyanidins consists of oligomeric proanthocyanidin having an overall degree of polymerization of 4 to 20;

the composition of oligomeric proanthocyanidins is substantially free of monomeric tannin base units and monomeric polyphenols; and the effective amount of the composition of oligomeric proanthocyanidins is an amount effective to agglutinate bacteria that cause a urinary tract infection such that the agglutinated bacteria are cleared from the urinary tract upon voiding of the bladder;

thereby treating or inhibiting the urinary tract infection.

* * * * *